(12) United States Patent
Deligianni et al.

(10) Patent No.: US 11,754,550 B2
(45) Date of Patent: Sep. 12, 2023

(54) MEDICAL DEVICE FOR STIMULATING AND SENSING BIOACTIVITY

(71) Applicant: International Business Machines Corporation, Armonk, NY (US)

(72) Inventors: Harikilia Deligianni, Alpine, NJ (US); Bruce B. Doris, Slingerlands, NY (US); Steven J. Holmes, Ossining, NY (US); Emily R. Kinser, Poughkeepsie, NY (US); Qinghuang Lin, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 1380 days.

(21) Appl. No.: 16/045,987

(22) Filed: Jul. 26, 2018

(65) Prior Publication Data
US 2020/0033322 A1    Jan. 30, 2020

(51) Int. Cl.
*G01N 33/487* (2006.01)
*B01L 3/00* (2006.01)
*C12Q 1/00* (2006.01)

(52) U.S. Cl.
CPC .. *G01N 33/48735* (2013.01); *B01L 3/502715* (2013.01); *C12Q 1/001* (2013.01); *G01N 33/48785* (2013.01); *G01N 33/48792* (2013.01); *B01L 2300/023* (2013.01); *B01L 2300/0645* (2013.01); *B01L 2300/123* (2013.01)

(58) Field of Classification Search
CPC ....... G01N 33/48735; G01N 33/48785; G01N 33/48792; B01L 3/502715; B01L 2300/023; B01L 2300/0645; B01L 2300/123; C12Q 1/001
See application file for complete search history.

(56) References Cited

U.S. PATENT DOCUMENTS

| | | | |
|---|---|---|---|
| 2006/0003310 A1* | 1/2006 | Klauke | G01N 33/48728 435/4 |
| 2014/0061049 A1* | 3/2014 | Lo | G01N 27/44704 204/547 |
| 2015/0305643 A1 | 10/2015 | Negi et al. | |
| 2017/0122928 A1 | 5/2017 | Naughton et al. | |
| 2017/0165471 A1 | 6/2017 | Baughman et al. | |
| 2018/0035934 A1 | 2/2018 | Kiani et al. | |

* cited by examiner

*Primary Examiner* — Dennis White
(74) *Attorney, Agent, or Firm* — Stephanie L. Carusillo

(57) ABSTRACT

In an approach, a biomedical device comprises at least one electrode, wherein the at least one electrode is coupled with a computer chip; at least two chemical sensors, wherein the at least two chemical sensors are coupled with the computer chip; the computer chip, wherein the computer chip comprises: a semiconductor substrate, and a processor; a microfluidic structure, wherein the microfluidic structure is an inert elastomeric polymer; a power supply device coupled to the computer chip; and an antenna configured to send data collected onto the computer chip to a remote server. In an approach, a processor stimulating a cell sample. A processor senses the presence of at least two types of biomolecules released by the cell sample. A processor records data collected by the at least two chemical sensors. A processor sends the recorded data to a remote server.

9 Claims, 6 Drawing Sheets

MEDICAL DEVICE FOR STIMULATING AND SENSING BIOACTIVITY

BACKGROUND

The present invention relates generally to the field of medical devices, and more particularly to biomedical sensors.

Cell membranes in the human body can maintain a membrane potential that ranges from −40 mV to −80 mV. This causes the interior of the cell has a different voltage than the exterior of the cell. When the cell becomes excited, ion channels in the cell membrane open, allowing ions such as Cl— to enter the cell. This leads to the depolarization of the cell membrane and starts the propagation of an electrical signal down the length of the cell. Certain cells in the body are electrically excitable cells: they respond to an electrical stimulus by depolarizing. This leads to an electrical signal that propagates down the length of the cell. This electrical signal triggers the release of certain biomolecules by the cell. This can be seen most commonly with neurons and endocrine cells within the body. The activity of a cell can be characterized by the voltage differential across the cell membrane, depolarized or not, and by characterizing the release of any biomolecules by the cell.

Neurons are nervous system cells that carry nerve impulses to and from the brain and spinal cord by using chemical substances called neurotransmitters to communicate an impulse from cell to cell. Neurotransmitters can change the electrical threshold needed for an electrical signal to pass through a neuron, impacting the neuron's activity by exciting or inhibiting the neuron. Neurons are often placed one directly after the other, with a small gap between one neuron and the next. When a neuron receives an electrical signal, the neuron releases neurotransmitters into that small gap. The next neuron then binds those neurotransmitters using neurotransmitter receptors. If the neurotransmitters are excitatory, the next neuron will also become activated and release neurotransmitters as well. If the neurotransmitters are inhibitory, then the next neuron will not be activated and will not release neurotransmitters. Neurotransmitter sensors analyze the communication between clusters of neurons in order to characterize the activity and function of neurons.

SUMMARY

Aspects of an embodiment of the present invention disclose an apparatus for a biomedical device comprising: at least one electrode, wherein the at least one electrode is coupled with a computer chip; at least two chemical sensors, wherein the at least two chemical sensors are coupled with the computer chip; the computer chip, wherein the computer chip comprises: a semiconductor substrate, and a processor; a microfluidic structure, wherein the microfluidic structure is an inert elastomeric polymer; a power supply device coupled to the computer chip; and an antenna configured to send data collected onto the computer chip to a remote server.

Aspects of an embodiment of the present invention disclose a method and computer system. A processor stimulates a cell sample. A processor senses the presence of at least two types of biomolecules released by the cell sample. A processor records data collected by the at least two chemical sensors. A processor sends the recorded data to a remote server.

DETAILED DESCRIPTION

Embodiments of the present invention recognize the importance of characterizing the real-time activity of a cell in order to gain a deeper understanding of how information is transmitted within the body. Cellular activity can often be characterized by the voltage differential across the cell membrane as a result of an electrical impulse or by characterizing the release of biomolecules as a result of an electrical impulse. However, using current technology, it is not possible to stimulate a cell and analyze the resulting activity of that same cell. Thus, embodiments of the present invention recognize that there is a need for an approach that enables characterization of real-time activity from a single cell. Embodiments of the present invention recognize solutions for characterizing the real-time activity of a single cell by using a biomedical sensor on cell samples that can stimulate a single cell and then analyze the subsequent reaction of the cell, including characterizing the voltage differentials and any biomolecules released. For example, this biomedical device can be used to stimulate a single neuron, measure the voltage differential across the cell membrane, and characterize the neurotransmitters released as a result of that stimulation. In this manner, as discussed in greater detail herein, embodiments of the present invention provide a way to measure the real-time activity of a single cell by using a stimulating electrode that can stimulate and sense the voltage differential across a single cell and using chemical sensors to detect biomolecules released by the cell as a result of the stimulation.

The present invention will now be described in detail with reference to the Figures.

Figure 1:
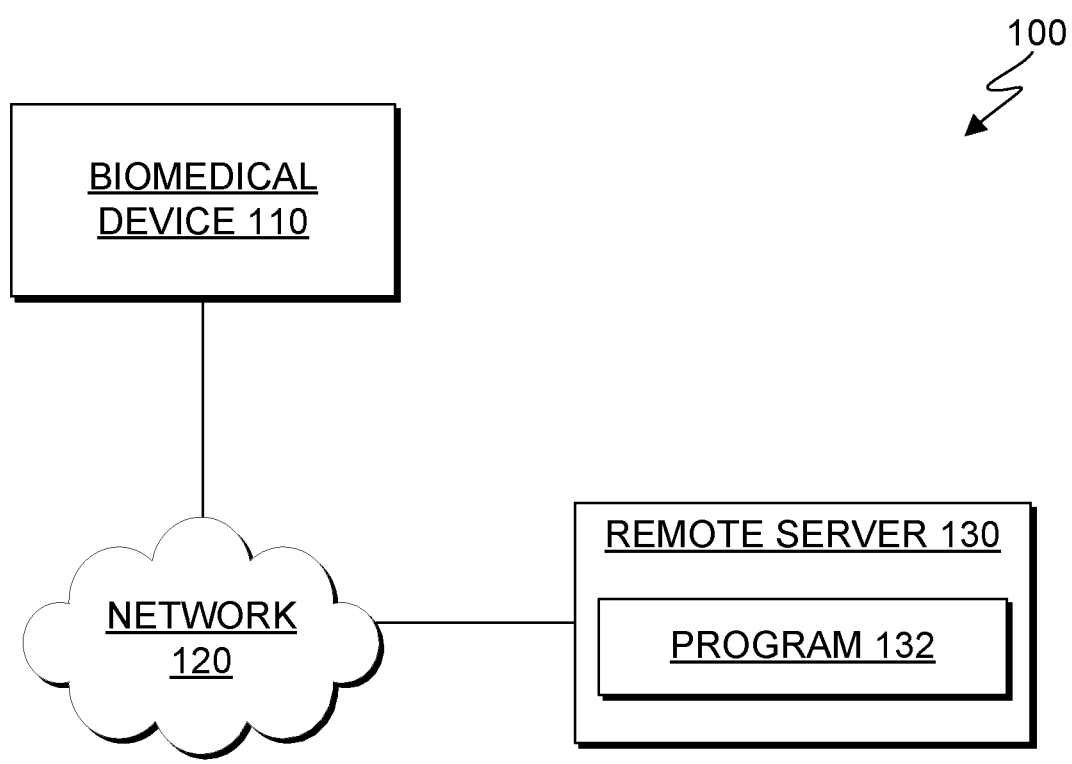
FIG. 1 depicts a block diagram of a biomedical environment, in accordance with an embodiment of the present invention.

FIG. 1 depicts a functional block diagram illustrating biomedical environment 100, in accordance with an embodiment of the present invention. FIG. 1 provides only an illustration of one embodiment and does not imply any limitations with regard to the environments in which different embodiments may be implemented. In the depicted embodiment, biomedical environment 100 includes biomedical device 110 and remote server 130, interconnected over network 120. Network 120 can be, for example, a local area network (LAN), a wide area network (WAN) such as the Internet, or a combination of the two, and can include wired, wireless, or fiber optic connections. In general, network 120 can be any combination of connections and protocols that will support communications between biomedical device 110 and remote server 130. Biomedical environment 100 may include additional biomedical devices, servers, computers or other devices not shown.

Remote server 130 operates to receive and store data collected by biomedical device 110. In an embodiment, remote server 130 includes program 132. In an embodiment, remote server 130 receives data collected by biomedical device 110 over network 120. Remote server 130 may be a management server, a web server, or any other electronic device or computing system capable of receiving and sending data. In some embodiments, remote server 130 may be a laptop computer, tablet, computer, netbook computer, personal computer (PC), a desktop computer, a smart phone, or any programmable electronic device capable of communicating with biomedical device 110 via network 120. In other embodiments, remote server 130 represents a server computing system utilizing multiple computers as a server system, such as in a cloud computing environment. In an embodiment, remote server 130 comprises one or more displays that can present one or more outputs generated by biomedical device 110. Remote server 130 may include components as depicted and described in further detail with respect to FIG. 5.

Program 132 operates to direct biomedical device 110 in characterizing the activity of a cell. In an embodiment, program 132 sends program instructions to biomedical device 110 to stimulate the cell. In an embodiment, program 132 sends program instruction to biomedical device 110 to sense the presence of biomolecules. In an embodiment, program 132 sends program instruction to biomedical device 110 to transmit data collected to the remote server. In some embodiments, program 132 resides on remote server 130. In other embodiments, program 132 may reside on another server, or another computing device, provided that program 132 can communicate with biomedical device 110.

Biomedical device 110 operates to characterize the activity of a cell by triggering an electrical impulse within the cell, measuring the voltage differential across the cell membrane, and characterizing any biomolecules released by the cell in response to the electrical impulse. For example, biomedical device 110 characterizes the real-time activity of a neuron by stimulating the neuron and tracking the voltage differential across the neuronal membrane, as well as by characterizing the neurotransmitters released by the neuron. In an embodiment, biomedical device 110 is inserted in vivo to measure the activity of a cell. For example, biomedical device 110 can be inserted into a human brain to measure the activity of a single neuron. In another embodiment, biomedical device 110 is used in vitro, where a biological sample is placed on a top surface of biomedical device 110.

Figure 2A:
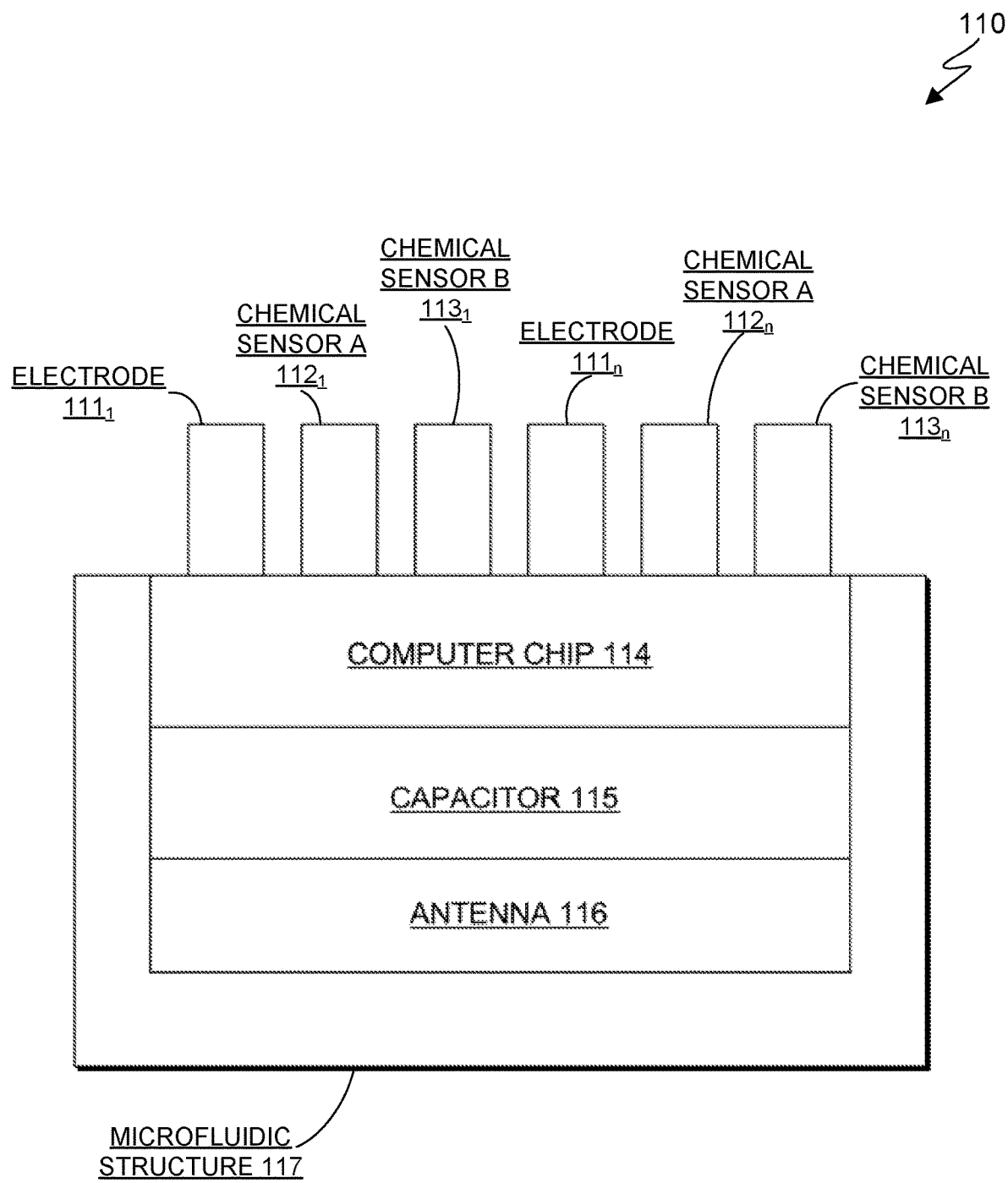
FIG. 2A depicts a side view of a biomedical device, in accordance with an embodiment of the present invention.

FIG. 2A depicts a side view of a functional block diagram of biomedical device 110 in accordance with an embodiment of the present invention. FIG. 2A provides only an illustration of one embodiment and does not imply any limitations with regard to the environments in which different embodiments may be implemented. In the depicted embodiment, biomedical device 110 comprises electrodes $111_1$ to $111_n$, chemical sensors A $112_1$ to $112_n$, chemical sensors B $113_1$ to $113_n$, computer chip 114, power supply device 115, antenna 116, and microfluidic structure 117.

Electrodes $111_1$ to $111_n$, where n is a total number of electrodes on biomedical device 110, operate to stimulate a cell by triggering an electrical impulse within the cell. Electrodes $111_1$ to $111_n$ also operate to sense the voltage differential across the cell membrane, which functions as a way to detect the electrical impulse as it travels through the cell. Electrode 111 refers to one instance of electrodes $111_1$ to $111_n$. In an embodiment, biomedical device 110 has one electrode 111 that is operatively connected to a top surface of computer chip 114. In another embodiment, biomedical device 110 has an array of electrodes $111_1$ to $111_n$ that are operatively connected to a top surface of computer chip 114. In this embodiment, the array of electrodes $111_1$ to $111_n$ allow for stimulation of different parts of a cell. For example, electrodes $111_1$ to $111_n$ can be arranged in a way to stimulate to two different points of a neuron's cell body. In an embodiment, electrode 111 has stimulatory capabilities to cause an electrical impulse within a cell. In another embodiment, electrode 111 has sensory capabilities to measure a voltage differential across a cell membrane of a cell. In yet another embodiment, electrode 111 has both stimulatory and sensory capabilities to stimulate a cell and measure a voltage differential across the cell membrane of the stimulated cell. For example, electrode $111_1$ stimulates a neuron, causing an electrical impulse, and electrode $111_2$ senses a resulting voltage differential across the cell membrane.

Chemical sensors A $112_1$ to $112_n$, where n is a total number of chemical sensors on biomedical device 110, operate as sensors to detect the presence of a first type of biomolecules released by a cell. In an embodiment, chemical sensors A $112_1$ to $112_n$ are operatively connected to a top surface of computer chip 114. Chemical sensor A 112 refers to one instance of chemical sensors A $112_1$ to $112_n$. In multiple embodiments, chemical sensor A $112_1$ to $112_n$ are amperometric sensors and/or resistivity sensors.

Chemical sensors B $113_1$ to $113_n$, where n is a total number of chemical sensors 113 B on biomedical device 110, operate as sensors to detect the presence of a second type of biomolecule released by the cell. In an embodiment, chemical sensors B $113_1$ to $113_n$ are operatively connected to a top surface of computer chip 114. Chemical sensor B 113 refers to one instance of chemical sensors B $113_1$ to $113_n$. In multiple embodiments, chemical sensor B $113_1$ to $113_n$ are amperometric sensors and/or resistivity sensors.

Amperometric chemical sensors characterize the presence of biomolecules based on an electrical current arising from the chemical interaction between the bioenzyme and biomolecule; the concentration of biomolecules can be characterized by the strength of the current. Amperometric sensors are created by growing a conductive polymer on an electrode in the presence of a bioenzyme. That bioenzyme is embedded into the polymer and also coats the electrode. A current is created when the bioenzyme interacts with a corresponding biomolecule in the environment. The measured current is indicative of the concentration of the biomolecule.

In an embodiment, chemical sensor A 112 is an amperometric sensor covered in bioenzyme A, which interacts with biomolecule A. In the same embodiment, chemical sensor A 112 detects an electrical current as bioenzyme A interacts with biomolecule A. For example, chemical sensor A 112 can detect the presence of different neurotransmitters based on the specific bioenzymes covering an electrode of the chemical sensor. In an example, chemical sensor A 112 is covered in bioenzyme acetylcholinesterase, which interacts with neurotransmitter acetylcholine and causes an electrical current that is detected by chemical sensor A 112.

In an embodiment, chemical sensor B 113 is an amperometric sensor covered in bioenzyme B, which interacts with biomolecule B. In the same embodiment, chemical sensor B 113 detects an electrical current as bioenzyme B interacts with biomolecule B. For example, chemical sensor B 113 can detect the presence of different neurotransmitters based on the specific bioenzymes covering the electrode of each sensor. In an example, chemical sensor B 113 is covered in glutamate oxidase, which interacts with the neurotransmitter glutamate, causing an electrical current that is detected by chemical sensor B 113.

Resistivity sensors characterize the presence of a biomolecule that does not interact with a bioenzyme by taking resistivity measurements. Resistivity sensors are created by growing a conductive polymer on an electrode in the presence of a biomolecule. The biomolecule is embedded in the polymer. Before use, the biomolecule is washed out of the polymer, creating cavities where biomolecules used to be embedded. In an environment containing those biomolecules, the resistivity of the sensor changes, due to the biomolecules binding to the cavities in the sensor. The measured resistivity is indicative of the concentration of the biomolecule.

In an embodiment, chemical sensor A 112 is created in the presence of biomolecule C, which is then washed out of the sensor before use, leaving behind cavities in the sensor. When chemical sensor A 112 is placed in an environment containing biomolecule C, the resistivity detected by the sensor changes due to biomolecule C from the environment binding to the cavities in chemical sensor A 112. For example, chemical sensor A 112 is created in the presence of dopamine. Before use, the dopamine is washed out of the sensor, leaving behind cavities in chemical sensor A 112. When dopamine is present, the dopamine binds to the cavities in chemical sensor A 112, changing the resistivity of the sensor.

In an embodiment, chemical sensor B 113 is created in the presence of biomolecule D, which is then washed out of the sensor before use, leaving behind cavities in the sensor. When chemical sensor B 113 is placed in an environment containing biomolecule D, the resistivity detected by the sensor changes due to biomolecule D from the environment binding to the cavities in chemical sensor B 113. For example, chemical sensor B 113 is created in the presence of epinephrine. Before use, the epinephrine is washed out, leaving behind cavities in chemical sensor B 113. When epinephrine is present, the epinephrine binds to the cavities, changing the resistivity of the sensor.

Computer chip 114 operates to record and store data collected by electrodes $111_1$ to $111_n$, chemical sensors A $112_1$ to $112_n$, and chemical sensors B $113_1$ to $113_n$ of biomedical device 110. In the depicted embodiment, computer chip 114 is operatively connected to electrodes $111_1$ to $111_n$, chemical sensors A $112_1$ to $112_n$, chemical sensors B $113_1$ to $113_n$, and power supply device 115. The dimensions of computer chip 114 can vary based on the desired functionality of biomedical device 110. For example, dimensions of computer chip 114 can range from, but not limited to, greater than or equal to 100×100 µm and less than or equal to 1000×1000 µm. In an embodiment, computer chip 114 comprises a processor and a semiconductor substrate, which can support one or more features of the biomedical device 110. Example materials that can comprise the semiconductor substrate can include, but are not limited to: silicon, germanium, silicon carbide, carbon doped silicon, compound semiconductors (e.g., comprising elements from periodic table groups III, IV, and/or V), silicon oxide, or a combination thereof. In another embodiment, the semiconductor substrate can comprise electronic structures, such as isolation wires. In an embodiment, semiconductor substrate can be transparent and/or semi-transparent to facilitate the operation of chemical sensors A $112_1$ to $112_n$, chemical sensors B $113_1$ to $113_n$ and/or electrodes $111_1$ to $111_n$. In yet another embodiment, the semiconductor substrate can comprise conductive material to facilitate the operation of chemical sensors A $112_1$ to $112_n$, chemical sensors B $113_1$ to $113_n$, and/or electrodes $111_1$ to $111_n$. The processor operates to facilitate execution of one or more computer readable program instructions. Example processors can comprise, but are not limited to: microcontrollers, microprocessors, microcomputers, field-programmable gate arrays ("FPGA"), and/or a combination thereof. In an embodiment, the processor can be operatively coupled to chemical sensors A $112_1$ to $112_n$, chemical sensors B $113_1$ to $113_n$, and electrodes $111_1$ to $111_n$ via one or more electrical connections. In an embodiment, the processor can analyze data collected by chemical sensors A $112_1$ to $112_n$, chemical sensors B $113_1$ to $113_n$, and/or control stimulation by electrodes $111_1$ to $111_n$.

Antenna 116 operates to send data collected and stored on computer chip 114 to a remote server, such as remote server 130. In an embodiment, antenna 116 is operatively connected to computer chip 114 and/or power supply device 115. In an embodiment, antenna 116 can facilitate connection between biomedical device 110 and network 120. For example, antenna 116 facilitates the transmission of data from biomedical device 110 to remote server 130 over network 120.

Power supply device 115 operates as a power supply for computer chip 114 to enable operation of chemical sensors A $112_1$ to $112_n$, chemical sensors B $113_1$ to $113_n$, and electrodes $111_1$ to $111_n$. In an embodiment, power supply device 115 can be operatively coupled to computer chip 114. Power supply device 115 can comprise but is not limited to: one or more capacitors and/or one or more batteries. In an embodiment, power supply device 115 is charged wirelessly, for example, through the use of one or more inducers.

Microfluidic structure 117 comprises a bioinert elastomeric polymer and is provided on a plurality of the sides of biomedical device 110. In the depicted embodiment, microfluidic structure 117 comprises two wall portions extending (e.g., in the vertical direction) substantially perpendicular to a base portion (e.g. extending in the horizontal direction), wherein antenna 116, power supply device 115, and computer chip 114 can be located on top of the base portion and/or between the wall portions. In an embodiment, microfluidic structure 117 is embedded with biomolecules to provide camouflage against biological defense mechanisms. In an embodiment, microfluidic structure 117 provides tabs and/or protrusions that are utilized to affix biomedical device 110 to cell samples. In an embodiment, microfluidic structure 117 houses a chemical delivery system, comprising of microfluidic channels extending along the vertical direction, within one or more wall portions of the structure. In an embodiment, the distal end of the microfluidic channel comprising the chemical delivery system is exposed to the tissue and/or environment surrounding the biomedical device 110. In an embodiment in which microfluidic structure 117 is used to stimulate a cell, the chemical delivery system is loaded with one or more hydrogels comprised of one or more biomolecules to be distributed to a cell, stimulating the cell. In this embodiment, the one or more hydrogels degrades slowly, allowing for the timed-release of the biomolecules. For example, the chemical delivery system of microfluidic structure 117 stores neurotransmitter that are distributed to a neuron, stimulating the neuron and causing an electrical impulse.

The dimensions of microfluidic structure 117 can vary according to the desired function of biomedical device 110 and/or the environment in which biomedical device 110 is placed. In an embodiment, the dimensions of microfluidic structure 117 also varies depending on the type of polymer used. In one embodiment, the length of microfluidic 117

(e.g., along the horizontal direction) can range from, but is not limited to, greater than or equal to 5 μm or less than or equal to 180 μm. In another embodiment, the height of microfluidic structure 117 (e.g., along the vertical direction) can range from, but is not limited to, greater than or equal to 1 millimeter (mm) and less than or equal to 2 mm. In another embodiment, the respective length (e.g., along the horizontal direction) of the microfluidic structure's 117 wall portions can range from, but is not limited to, greater than or equal to 30 μm and less than or equal to 3000 μm. In yet another embodiment, the thickness of the microfluidic structure can range from, but is not limited to, greater than or equal to 0.3 mm and less than or equal to 10 mm.

Figure 2B:
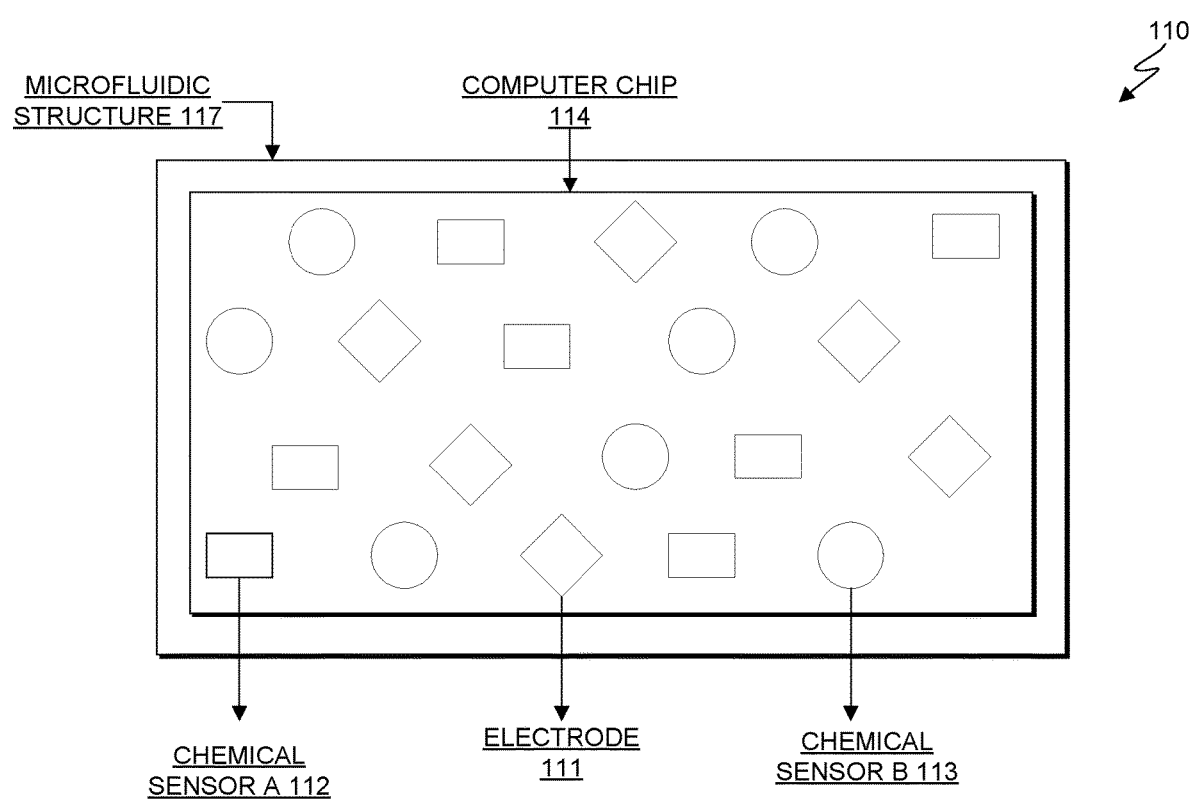
FIG. 2B depicts top view of a biomedical device, in accordance with an embodiment of the present invention.

FIG. 2B depicts a top view of a functional block diagram of biomedical device 110 in accordance with an embodiment of the present invention. In the depicted embodiment, electrodes $111_1$ to $111_n$, chemical sensors A $112_1$ to $112_n$, and chemical sensors B $113_1$ to $113_n$ are arrayed across the top surface of computer chip 114, which is encased in microfluidic structure 117. This structure allows biomedical device 110 to stimulate different parts of a cell and detect biomolecules being released by the cell.

Figure 3:
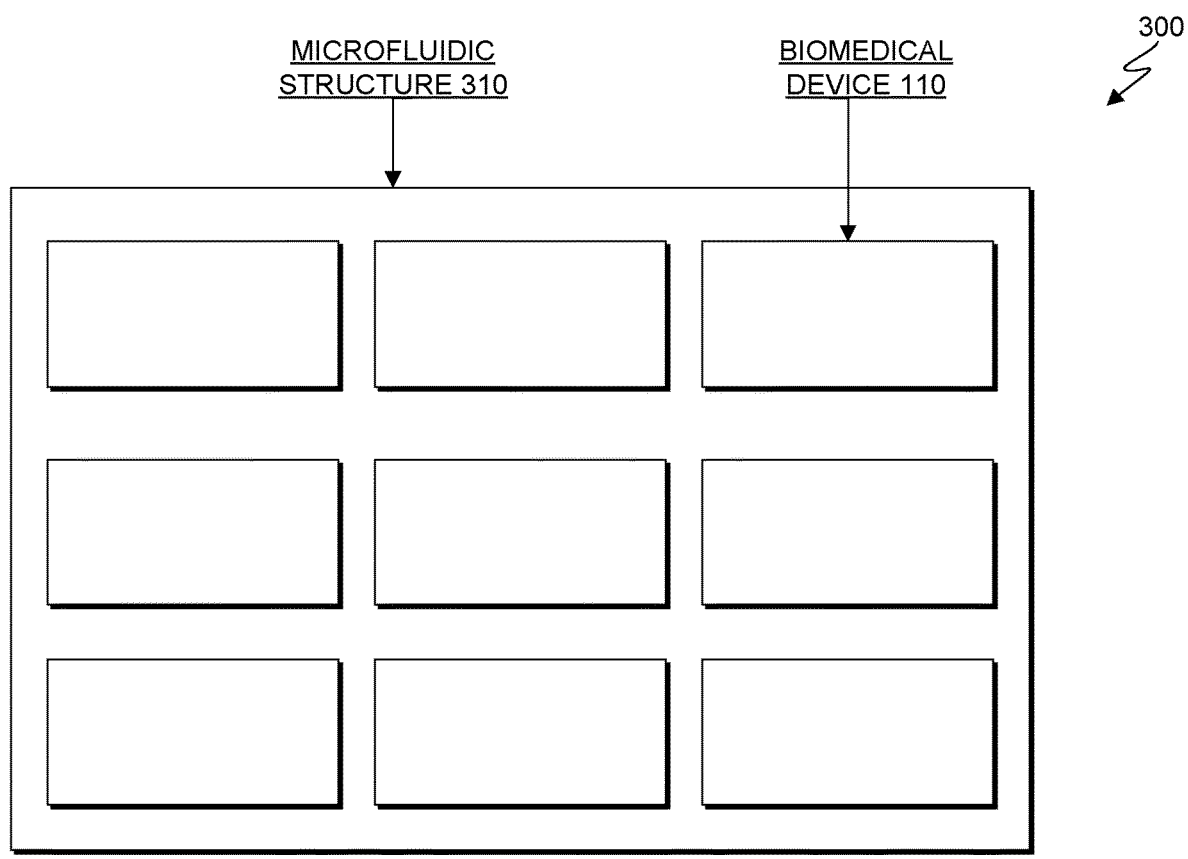
FIG. 3 depicts a top view of an array of biomedical devices, in accordance with an embodiment of the present invention.

FIG. 3 depicts a top view of a function block diagram of biomedical device 200 in accordance with another embodiment of the present invention. In this embodiment, biomedical device 300 contains multiple biomedical devices 110, as described in FIGS. 2A and 2B, encased in microfluidic structure 310, which is functionally the same as microfluidic structure 117 described in FIGS. 2A and 2B. In an embodiment, biomedical device 300 may be inserted in vivo or in vitro to collect data on multiple cells while characterizing the real-time activity of each individual cell.

Figure 4:
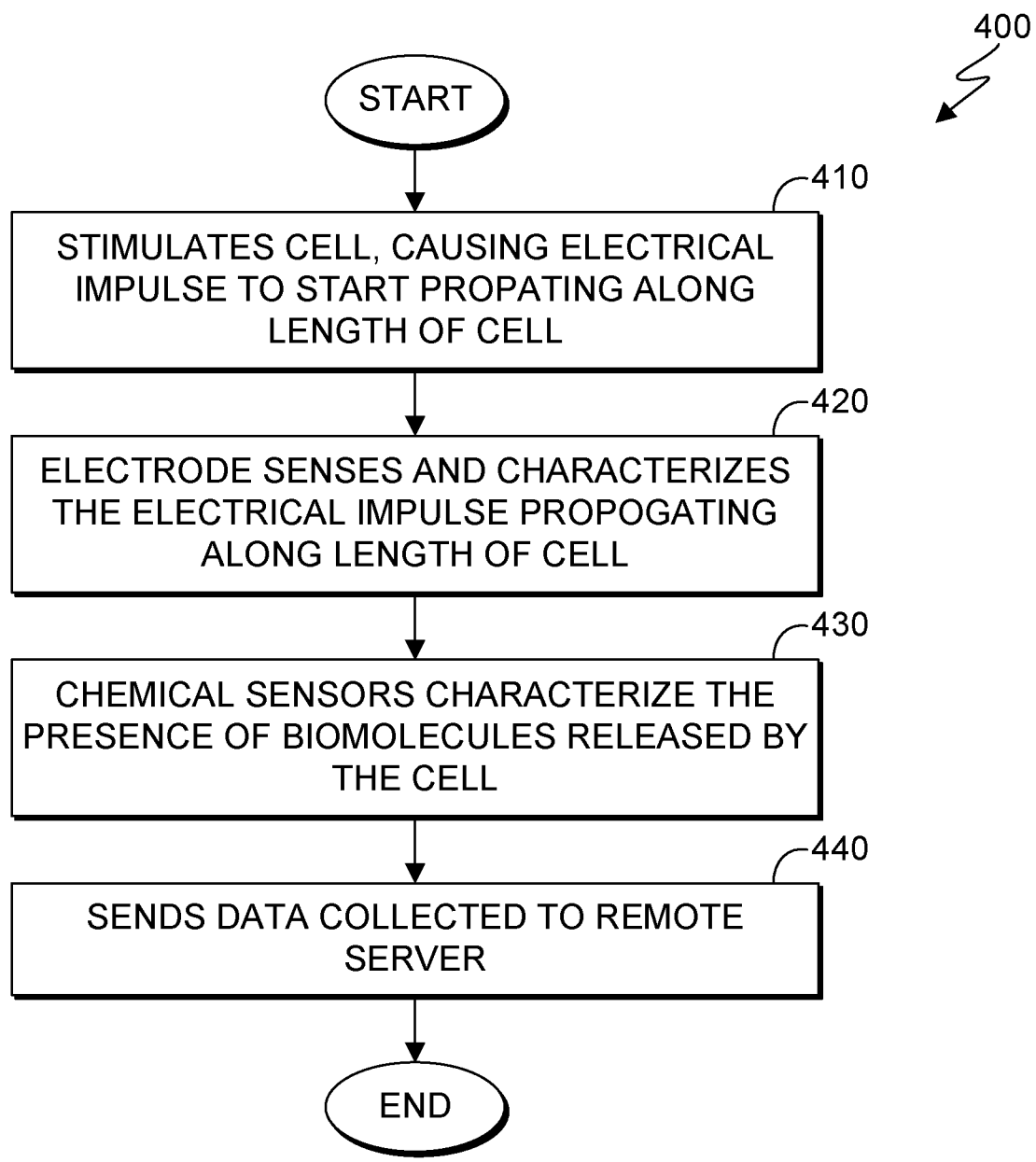
FIG. 4 depicts a flow chart of the steps of a program of the biomedical environment, in accordance with an embodiment of the present invention.

FIG. 4 depicts a flowchart 400 of the steps of program 132, executing within biomedical environment 100 depicted in FIG. 1, in accordance with an embodiment of the present invention. In an embodiment, program 132 sends program instructions to biomedical device 110 to characterize the real-time activity of a cell by stimulating the cell, sensing a voltage differential across the cell membrane, and detecting and characterizing the presence of biomolecules released by the cell in response to the stimulation. It should be appreciated that the process depicted in FIG. 4 illustrates one possible iteration of program 132, which repeats for each stimulation performed on cell samples.

In step 410, program 132 sends program instructions to biomedical device 110 to stimulate a cell, causing an electrical impulse to propagate within the cell. In an embodiment, electrode 111 of biomedical device 110 stimulates the cell by sending out an electrical current that depolarizes the cell membrane. The cell membrane depolarization causes an electrical impulse within the cell. In another embodiment, microfluidic structure 117 of biomedical device 110 stimulates the cell by releasing biomolecules stored within the structure, which travel across the cell membrane and trigger an electrical impulse within the cell. In yet another embodiment, both electrode 111 and microfluidic structure 117 stimulate the cell.

In optional step 420, program 132 sends program instructions to biomedical device 110 to sense a voltage differential. In an embodiment, electrode 111 of biomedical device 110 senses a voltage differential arising from the stimulated cell. In an embodiment, in which electrode 111 of biomedical device 110 has both stimulating and sensory capabilities, electrode 111 causes the electrical impulse within the cell, as depicted in step 410, and senses a subsequent voltage differential arising within the same cell. In another embodiment, an electrode $111_1$ that senses a voltage differential is a different electrode from an electrode $111_2$ that stimulated the cell. In an embodiment, computer chip 114 records the voltage differential sensed by electrode 111.

In step 430, program 132 sends program instructions to biomedical device 110 to detect and characterize the presence of biomolecules released by the stimulated cell. In an embodiment, chemical sensor A 112 and/or chemical sensor B 113 of biomedical device 110 are amperometric sensors that detect and characterize the presence of biomolecules released by the stimulated cell based on an electrical current. In an embodiment, program 132 sends program instructions to computer chip 114 to record the electrical current detected by chemical sensor A 112 and/or chemical sensor B 113. In another embodiment, chemical sensor A 112 and/or chemical sensor B 113 are resistivity sensors that detect and characterize the presence of biomolecules based on the change in resistivity of the sensor. In an embodiment, program 132 sends program instructions to computer chip 114 to record the resistivity sensed by chemical sensor A 112 and/or chemical sensor B 113.

In step 440, program 132 sends program instructions to biomedical device 110 to send data collected in steps 420 and 430 to a remote server. The data collected includes the voltage differential sensed by electrode 111, the electrical currents detected by chemical sensor A 112 and/or chemical sensor B 113, and the resistivity sensed by chemical sensor A 112 and/or chemical sensor B 113. In an embodiment, antenna 116 of biomedical device 110 sends data recorded by computer chip 114 to remote server 130 over network 120.

Figure 5:
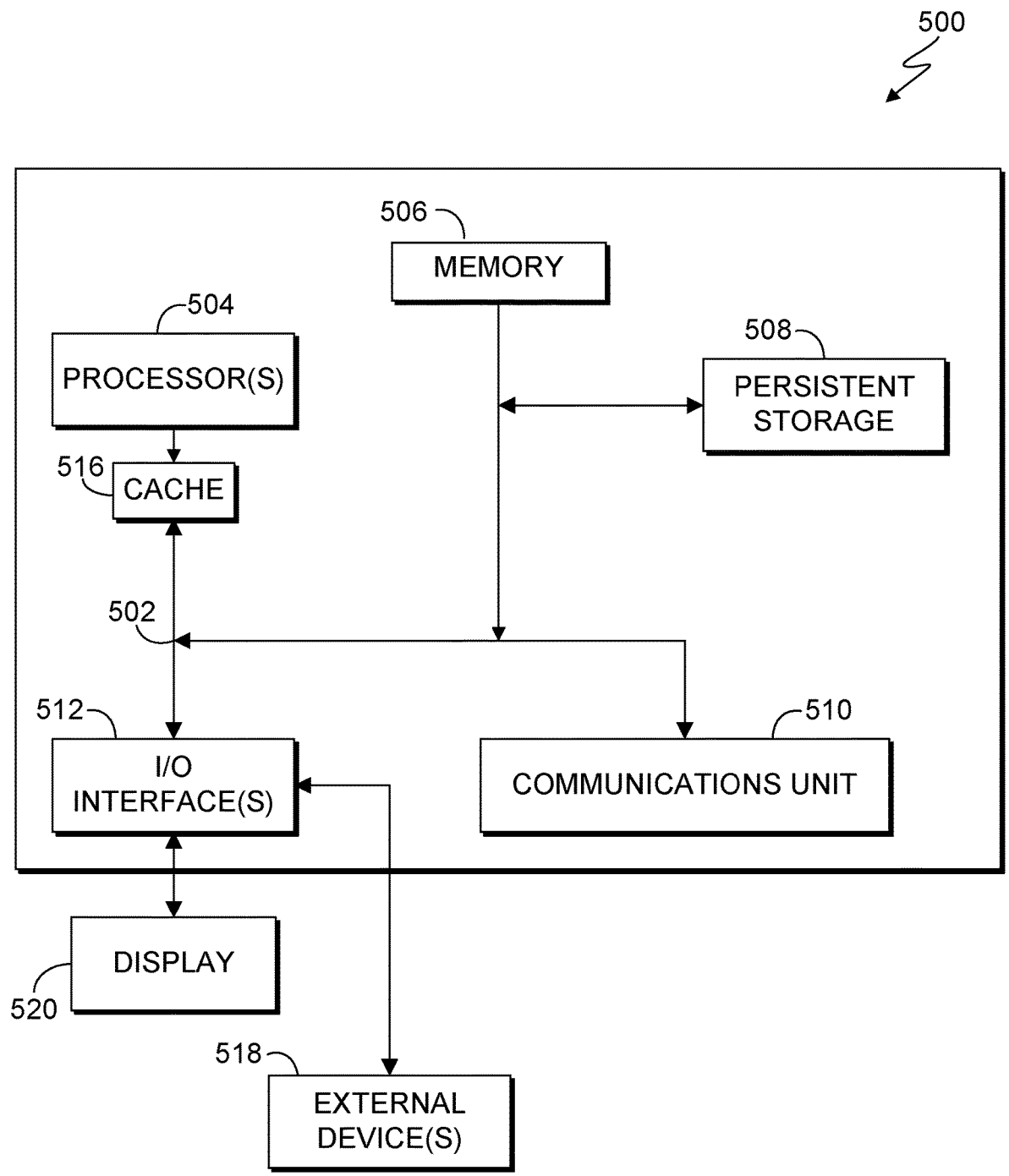
FIG. 5 depicts a block diagram of a computing device of biomedical environment, in accordance with an embodiment of the present invention.

FIG. 500 depicts a block diagram of computer 500 suitable for remote server 130, in accordance with an illustrative embodiment of the present invention. It should be appreciated that FIG. 5 provides only an illustration of one implementation and does not imply any limitations with regard to the environments in which different embodiments may be implemented. Many modifications to the depicted environment may be made.

Computer 500 includes communications fabric 502, which provides communications between cache 516, memory 506, persistent storage 508, communications unit 410, and input/output (I/O) interface(s) 512. Communications fabric 502 can be implemented with any architecture designed for passing data and/or control information between processors (such as microprocessors, communications and network processors, etc.), system memory, peripheral devices, and any other hardware components within a system. For example, communications fabric 402 can be implemented with one or more buses or a crossbar switch.

Memory 506 and persistent storage 508 are computer readable storage media. In this embodiment, memory 506 includes random access memory (RAM). In general, memory 506 can include any suitable volatile or non-volatile computer readable storage media. Cache 516 is a fast memory that enhances the performance of computer processor(s) 504 by holding recently accessed data, and data near accessed data, from memory 506.

Programs may be stored in persistent storage 508 and in memory 506 for execution and/or access by one or more of the respective computer processors 504 via cache 516. In an embodiment, persistent storage 508 includes a magnetic hard disk drive. Alternatively, or in addition to a magnetic hard disk drive, persistent storage 508 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 508 may also be removable. For example, a removable hard drive may be used for persistent storage 508. Other examples include optical and magnetic disks, thumb drives, and smart cards that are inserted into a drive for transfer onto another computer readable storage medium that is also part of persistent storage 508.

Communications unit 510, in these examples, provides for communications with other data processing systems or devices. In these examples, communications unit 510 includes one or more network interface cards. Communications unit 510 may provide communications through the use of either or both physical and wireless communications links. Programs may be downloaded to persistent storage 508 through communications unit 510.

I/O interface(s) 512 allows for input and output of data with other devices that may be connected to server computer 102. For example, I/O interface 512 may provide a connection to external devices 518 such as a keyboard, keypad, a touch screen, and/or some other suitable input device. External devices 518 can also include portable computer readable storage media such as, for example, thumb drives, portable optical or magnetic disks, and memory cards. Software and data used to practice embodiments of the present invention can be stored on such portable computer readable storage media and can be loaded onto persistent storage 508 via I/O interface(s) 512. I/O interface(s) 512 also connect to a display 520.

Display 520 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. An apparatus for a biomedical device, the apparatus comprising:
   a computer chip, wherein the computer chip comprises:
     a semiconductor substrate, and
     a processor;
   at least one electrode, wherein the at least one electrode is coupled with a top side of the computer chip;
   at least two chemical sensors, wherein the at least two chemical sensors are coupled with the top side of the computer chip;
   a microfluidic structure, wherein the microfluidic structure is an inert elastomeric polymer, and wherein the microfluidic structure encases all but the top side of the computer chip;
   a power supply device coupled to the computer chip; and
   an antenna configured to send data collected onto the computer chip to a remote server.

2. The apparatus of claim 1, wherein the at least one electrode is configured to stimulate a cell sample.

3. The apparatus of claim 1, wherein the at least one electrode is configured to sense a voltage differential across a cell sample.

4. The apparatus of claim 1, wherein the at least one electrode is configured to stimulate a cell sample and sense a voltage differential across the cell sample.

5. The apparatus of claim 1, wherein a first chemical sensor of the at least two chemical sensors is an amperometric sensor covered in a first bioenzyme and a second chemical sensor of the at least two chemical sensors is an amperometric sensor covered in a second bioenzyme.

6. The apparatus of claim 1, wherein a first chemical sensor of the at least two chemical sensors is a resistivity sensor created in the presence of a first biomolecule and a second chemical sensor of the at least two chemical sensors is a resistivity sensor created in the presence of a second biomolecule.

7. The apparatus of claim 1, wherein a first chemical sensor of the at least two chemical sensors is an amperometric sensor covered in a first bioenzyme and a second chemical sensor of the at least two chemical sensors is a resistivity sensor created in the presence of a first biomolecule.

8. The apparatus in claim 1, wherein the computer chip is operatively coupled to the at least two chemical sensors and the at least one electrode.

9. The apparatus of claim 1, wherein the microfluidic structure comprises at least one channel to facilitate the release of biomolecules stored within the microfluidic structure used to stimulate a cell sample.

* * * * *